United States Patent
Morris et al.

(10) Patent No.: US 6,936,634 B2
(45) Date of Patent: Aug. 30, 2005

(54) RUTHENIUM (II) COMPOUNDS FOR USE IN THE THERAPY OF CANCER

(75) Inventors: Robert Edward Morris, Eire (IE); Peter John Sadler, Penicuik (GB); Duncan Jodrell, Edinburgh (GB); Haimei Chen, Edinburgh (GB)

(73) Assignee: The University Court, The University of Edinburgh (UK), Edinburgh (GB)

( * ) Notice: Subject to any disclaimer, the term of this patent is extended or adjusted under 35 U.S.C. 154(b) by 0 days.

(21) Appl. No.: 10/312,940

(22) PCT Filed: Jun. 26, 2001

(86) PCT No.: PCT/GB01/02824

§ 371 (c)(1),
(2), (4) Date: Aug. 15, 2003

(87) PCT Pub. No.: WO02/02572

PCT Pub. Date: Jan. 10, 2002

(65) Prior Publication Data

US 2004/0029852 A1 Feb. 12, 2004

(30) Foreign Application Priority Data

Jun. 30, 2000 (GB) .............................. 0016052

(51) Int. Cl.[7] .......................... A61K 31/28; C07F 15/00
(52) U.S. Cl. ......................... 514/492; 556/136; 556/137
(58) Field of Search ......................... 514/492; 556/136, 556/137

(56) References Cited

U.S. PATENT DOCUMENTS

| | | | |
|---|---|---|---|
| 4,699,978 A | 10/1987 | Barton | 536/27 |
| 4,843,069 A | 6/1989 | Keller et al. | 514/184 |
| 4,980,472 A | 12/1990 | Tomcufcik et al. | 544/405 |
| 5,225,556 A | 7/1993 | Barton | 546/88 |

FOREIGN PATENT DOCUMENTS

| | | |
|---|---|---|
| JP | 11209314 | 3/1999 |
| WO | WO 86/00804 | 2/1986 |
| WO | WO 96/13510 | 5/1996 |
| WO | WO 02/40494 | 5/2002 |

OTHER PUBLICATIONS

Aird et al., "In vitro and in vivo activity and cross resistance profiles of novel ruthemium (II) . . . " Brit. J. of Cancer 86:1652–1657, 2002.
Aird et al., "RM175, a novel ruthenium (Ru[II]) organo-metallic complex: patterns of resistance . . . " Brit. J. of Cancer 85 (suppl. 1):101, 2001.
Allardyce et al., "Ruthenium in Medicine: Current Clinical Uses and Future Prospects" Plat. Metals Rev. 45:62–69, 2001.
Allardyce et al., "[Ru($\eta^6$–p–cymene)Cl$_2$(pta)] . . . a water soluble compound that exhibits pH dependent DNA binding . . . " Chem. Commun. 15:1396–1397, 2001.

Aronson et al., "The reactions of Ru($\eta^6$–arene)Cl$_2$I$_2$ compounds with a series of aminopyridine ligands: . . . " Polyhedron 10:1727–1732, 1991.
Beasley et al., "Complexation of 1,4,5,8,9,10–Hexahydroanthracene (HHA) to iron or ruthenium . . . " Organometallics 12:4599–4606, 1993.
Bennett et al., "Arene ruthenium (II) complexes formed by dehydrogenation of cyclohexadiences . . . " J. Chem. Soc. 2:233–241, 1974.
Bennett et al., "Mono–and bis–(acetylacetonato) complexes of arene–ruthenium (II) and arene–osmium (II): . . . " J. Chem. 70:6555–660, 2001.
Carmona et al., "Synthesis, X–Ray Structure and Nuclear Magnetic Resonance . . . " J. Chem. Soc. Dalton Trans. 1463–1476, 1990.
Chen et al., "Organometallic ruthenium (II) Diamine anticancer complexes: . . . " J. Am. Chem. Soc. 124:3064–3082, 2002.
Cetinkaya et al., "Antibacterial and antifungal activities of complexes of ruthenium (II)" Arnzeim.–Forsch. 49:538–540, 1999.
Crabtree et al., "Arene–Ruthenium Complexes Containing Nitrogen Donor Ligands" J. of Organometallic Chem. 141:325–330, 1977.
Cummings et al., "Novel ruthenium (RuII) organo–metallic complexes: in vitro cytotoxicity . . . " Clinical Cancer Research 6 (suppl. 4494s) 2000.
Elsegood et al, "The synthesis of new paracyclophane complexes of ruthenium (II): . . . " J. of Organometallic Chem 356:C29–C31, 1988.
Garcia et al., "Reactivity of [{($\eta^6$–arene)RuCl($\mu$–Cl)}$_2$] towards some potentially bidentate ligands . . . " J. of Organometallic Chem. 467:119–126, 1994.
Gleichmann et al., "$\eta^3$–Pentamethylcyclopentadienyl-ruthenium (II) complexes containing . . . " J. Chem. Soc. Dalton Trans. 1549–1554, 1995.

(Continued)

Primary Examiner—Porfirio Nazario-Gonzalez
(74) Attorney, Agent, or Firm—Fish & Richardson, P.C.

(57) ABSTRACT

Compounds which may be used in the treatment and/or prevention of cancer have the formula (I): wherein R$^1$ and R$^2$ together with the ring to which they are bound represent a saturated or unsaturated carbocyclic or heterocyclic group

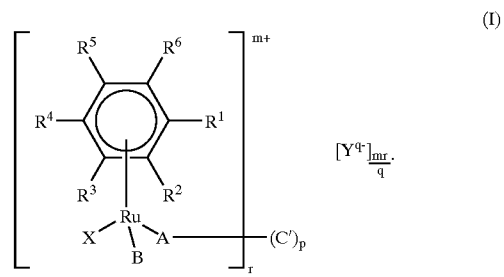

51 Claims, No Drawings

OTHER PUBLICATIONS

Gupta et al., "Synthesis, characterization, reactivity and structure of some mono and binuclear . . . " J. of Organometallic Chem. 568:13–20, 1998.

Hung et al., "Aquo Chemistry of Monoarene Complexes of Osmiium (II) and Ruthenium(II)" Inorganic Chem 20 457–463, 1981.

Jensen et al., "Facile preparation of $\eta^6$–p–cymene ruthenium diphosphine complexes." J. of Organometallic Chem. 556:151–158, 1998.

Korn et al., "Oligometic (n$^6$–arene) ruthenium (II) complexes of adenine and adenosime with N6; N7 coordination" Inorganica Chimica Acta 254:85–91, 1997.

Kramer, R., "Application of π–Arene–Ruthenium complexes in peptide labeling and peptide synthesis" Andew. Chem. Int. Ed. Engl. 35:1197–1199, 1996.

Morris et al., "Inhibition of cancer cell growth by ruthenium (II) arene complexes" J. Med. Chem. 44:3616–3621, 2001.

Muller et al., "($\eta^6$–Aren) ($\eta^4$–buta–1, 3–dien)ruthenium(0)–Komplexe: . . . "J. of Organometallic Chem 458:219–224, 1993.

Pandey et al., "Synthesis and characterization of [Ru($\eta^6$–C$_6$Me$_6$)Cl$_2$(CNPy)] and . . . " Indian J. of Chemistry 35A:434–437, 1996.

Pathak et al., "Synthesis and characterization of [{Ru($\eta^6$–C$_6$Me$_6$)Cl$_2$}2 ($\mu$–DCBT)] and its reaction . . . " Indian J. of Chem. 37A:165–168, 1998.

Pertici et al., "Synthesis of the Arene complex . . . " J. Chem. Soc. Dalton Trans 315–319, 1988.

Sheldrick et al., "Synthesis and structural characterization of $\eta^6$–arene–ruthenium (II) . . . " J. of Organometallic Chem. 377:357–366, 1989.

Sheldrick et al., "$\eta^3$–Pentamethycyclopentadienylruthenium (II) complexes containing . . . " J. of Organometallic Chem. 470:183–187, 1994.

Sheldrick et al., "Synthesis and structural characterization of $\eta^6$–Arene–ruthenium (II) complexes . . . " Onorganica Chimica Acta. 168:93–100, 1990.

Solorzano et al., "Preparation of arene ruthenium (II) complexes with activated ligands for protein labeling" Inorganic Chim. Acta 97:135–141, 1985.

Wolff et al., "($\eta^6$–Arene)ruthenium(II) labeling of amino acids and peptides . . . "Chemische Berichte–Recueil 130:981–988, 1997.

Wolff et al., "Bis(arene) ruthenium (II) complexes containing $\eta^6$–coordinated phenylalanine derivatives" J. or Organometallic Chem. 531:141–149, 1997.

Zelonka et al., "Benzene complexes of ruthenium (II)" Canadian J. of Chem. 50:3063–3072, 1972.

RUTHENIUM (II) COMPOUNDS FOR USE IN THE THERAPY OF CANCER

This invention relates to ruthenium (II) compounds, to their use in medicine, particularly for the treatment and/or prevention of cancer, and to a process for their preparation.

Certain ruthenium (II) complexes have been proposed for use in treating cancer. For example, U.S. Pat. No. 4,980,473 discloses 1,10-phenanthroline complexes of rutheniunm (II) and cobalt (III) which are said to be useful for the treatment of tumour cells in a subject.

Some other ruthenium (II) and ruthenium (III) complexes which have been shown to exhibit antitumour activity are mentioned in Guo et al, Inorganica Chimica Acta, 273 (1998), 1–7, specifically trans-[$RuCl_2(DMSO)_4$], trans-[$RuCl_2(imidazole)_2$]- and trans-[$RuCl_4(indazole)_2$]$^-$. Guo et at discloses that the most interesting feature of these complexes is their anti-metastatic activity. Clarke et al have reviewed the anticancer, and in particular the antimetastatic, activity of ruthenium complexes: Chem. Rev. 1999, 99, 2511–2533. Also, Sava has reviewed the antimetastatic activity in "Metal Compounds in Cancer Therapy" Ed by S P Fricker, Chapman and Hall; London 1994, p. 65–91.

Dale. et al, Anti-Cancer Drug Design (1992), 7, 3–14, describes a metronidazole complex of ruthenium (II) ie, [($\eta^6$-$C_6H_6$)$RuCl_2$(metronidazole)] and its effect on DNA and on *E. coli* growth rates. Metronidazole sensitises hypoxic tumour cells to radiation and appears to be an essential element of the complexes of Dale et al. There is no indication in Dale et al that the complexes would be at all effective in the absence of the metronidazole ligand.

Krämer et al, *Chem Eur J.*, 1996, 2, No. 12, p. 1518–1526 discloses half sandwich complexes of ruthenium with amino esters.

There exists a need for novel anti-cancer compounds which can be used as alternatives to the compounds which are currently available.

The present invention provides a novel class of ruthenium (II) complexes having anti-tumour activity.

According to the present invention there is provided a ruthenium (II) compound of formula (I):

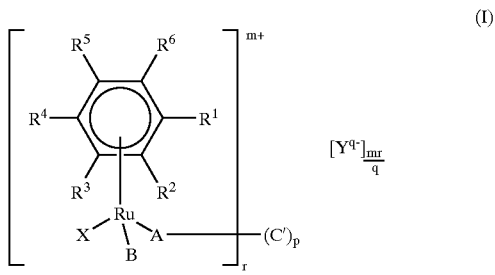

wherein $R^1$ and $R^2$ together with the ring to which they are bound represent a saturated or unsaturated carbocyclic or heterocyclic group containing up to three 3- to 8- membered carbocyclic or heterocyclic rings, wherein each carbocyclic or heterocyclic ring may be fused to one or more other carbocyclic or heterocyclic rings; and wherein each of the rings may be optionally substituted by one or more groups independently selected from alkyl, aryl, alkaryl, halo, carboxy, carboxyester, carboxyamide, sulfonate, sulfonido or alkether;

$R^3$, $R^4$, $R^5$ and $R^6$ independently represent H, alky, —$CO_2R'$, aryl or alkaryl, which latter two groups are optionally substituted on the aromatic ring;

R' represents alkyl, aryl or alkaryl;

X is halo, $H_2O$, (R') (R") S(O), $R'CO_2$ or (R') (R")C=O, where R" represents alkyl, aryl or alkaryl and R' is as defined above;

Y is a counterion;

m is 0 or 1;

q is 1, 2 or 3;

C' is $C_1$ to $C_{12}$ alkylene, optionally substituted in or on the alkylene chain, bound to two A groups;

p is 0 or 1 and r is 1 when p is 0 and r is 2 when p is 1; and

A and B are each independently O-donor, N-donor or S-donor ligands and one of A and B may be halo.

Suitably, A and B are each independently N-donor nitrile ligands; or B is halo and A is an N-donor pyridine ligand, optionally substituted at one or more of the carbon rings of the pyridine ring; or B is halo and A is an O-donor carboxylate ligand; or B is halo and A is an S-donor sulfonyl ligand; or p is 0, A is $NR^7R^8$ and B is $NR^9R^{10}$, wherein $R^7$, $R^8$, $R^9$ and $R^{10}$ independently represent H or alkyl, and A and B are linked by an alkylene chain, optionally substituted in or on the alkylene chain; or p is 1, A is $NR^7$ and B is $NR^9R^{10}$, wherein $R^7$, $R^9$ and $R^{10}$ are as previously defined, and A and B are linked by an alkylene chain, optionally substituted.

The compounds of the invention may be in the form of solvates and/or prodrugs. Prodrugs are variants of the compounds of the invention which can be converted to compounds of formula (I) in vivo.

The compounds of formula (I) may have one or more chiral centres. When the compounds of formula (I) have one or more chiral centres, they may be in the form of one enantiomer, may be enriched in one enantiomer or may be a racemic mixture.

The term "alkyl" as used herein includes $C_1$ to $C_6$ alkyl groups which may be branched or unbranched and may be open chain or, when they are $C_3$ to $C_6$ groups, cyclic. Unbranched open chain alkyl groups include, for example, methyl, ethyl, propyl, butyl, pentyl and hexyl. Branched open chain alkyl groups include, for example, 2-propyl, 2-butyl and 2-(2-methyl)propyl. Cyclic groups include cyclopropyl, cyclobutyl, cyclopentyl and cyclohexyl. The alkyl groups in the compounds of the invention may optionally be substituted. Substituents include one or more further alkyl groups and/or one or more further substituents, such as, for example, cyano, nitro, hydroxyl, haloalkyl, —$CO_2$alkyl, halo, thiol (SH), thioether (eg, S-alkyl) and sulfonate. The term "alkylene" is defined similarly to the definition of the term "alkyl" but includes $C_2$ to $C_{12}$ groups and is a divalent species with radicals separated by two or more (eg, from two to twelve) carbon atoms linked in a chain. Preferably, the alkylene groups are straight chain groups. Alkylene groups are optionally substituted in the akylene chain, preferably with one or more phenylene (eg, 1-4-phenylene) and/or —$CONR^{1a}$- groups and/or —$NR^{2a}$- groups, where $R^{1a}$ and $R^{2a}$ independently represent H, alkyl, aryl or alkaryl. Preferably, $R^{1a}$ and $R^{2a}$ are H or $C_1$ to $C_3$ alkyl.

The term "aryl" as used herein includes aromatic carbocyclic rings such as phenyl and naphthyl and heterocyclic rings such as pyridyl, imidazolyl, pyrrolyl and furanyl. Aryl groups may optionally be substituted with one or more substituents including, for example, alkyl, cyano, nitro, hydroxyl, haloalkyl, —$CO_2$alkyl, halo, thiol (SH), thioether (eg, S-alkyl) and sulfonate.

The term "alkaryl" means alkyl substituted with aryl eg, benzyl.

The term "alkether" means alkyl substituted with either —O— or —S— (eg, O-alkyl).

The term "halo" means a halogen radical selected from fluoro, chloro, bromo and iodo.

The term "haloalkyl" means alkyl substituted with one or more halo groups eg, trifluoromethyl.

The term "carboxyester" means —$CO_2$alkyl, —$CO_2$ aryl, —OCOalkyl or —OCOaryl, preferably —$CO_2$ alkyl or —OCOalkyl.

The term "heterocyclic ring" as used herein refers to a 3-, 4-, 5-, 6-, -7, or 8- (preferably 5-, 6- or 7-) membered saturated or unsaturated ring, which may be aromatic or non-aromatic, containing from one to three heteroatoms independently selected from N,O and S, eg, indole.

The term "carbocyclic ring" as used herein refers to a saturated or unsaturated ring, which may be aromatic or non-aromatic, containing from 3 to 8 carbon atoms (preferably 5 to 7 carbon atoms) and includes, for example, cyclopropyl, cyclobutyl, cyclopentyl, cyclohexyl and cycloheptyl.

In one aspect, $R^1$ and $R^2$ together with the ring to which they are bound in compounds of formula (I) may represent an ortho- or peri-fused carbocyclic or heterocyclic ring system.

$R^1$ and $R^2$ together with the ring to which they are bound may represent a wholly carbocyclic fused ring system such as a ring system containing 2 or 3 fused carbocyclic rings eg, optionally substituted, optionally hydrogenated naphthalene or anthracene.

In another aspect, $R^1$ and $R^2$ together with the ring to which they are bound in compounds of formula (I) may represent a fused tricyclic ring such as anthracene or a mono, di, tri, tetra or higher hydrogenated derivative of anthracene. For example, $R^1$ and $R^2$ together with the ring to which they are bound in formula (I) may represent anthracene, 1,4-dihydroanthracene or 1,4,9,10-tetrahydroanthracene.

In a further aspect, $R^1$ and $R^2$ together with the ring to which they are bound in formula (I) may represent:

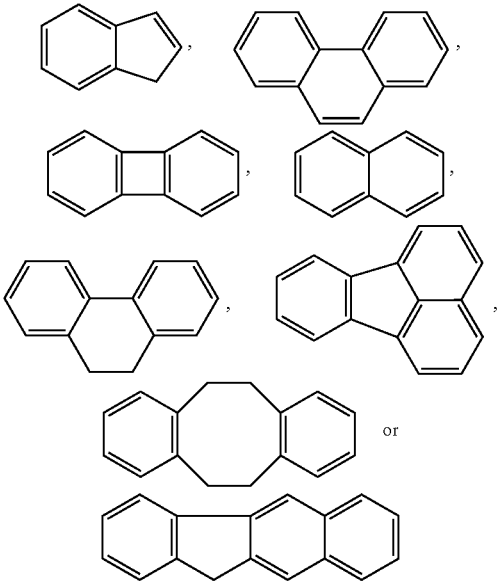

In the compounds of formula (I), $R^3$, $R^4$, $R^5$ and $R^6$ may represent H.

In one aspect, A and B in the compounds of formula (I) both represent $R^{11}$—CN. $R^{11}$ is alky, preferably $C_1$ to $C_3$ alkyl, more preferably methyl.

In another aspect, one of A and B in the compounds of formula (I) represents a $R^{12}R^{13}S(O)$ group and the other represents halo, preferably chloro. $R^{12}$ and $R^{13}$ are alkyl, preferably methyl.

In a further aspect, A and B may together represent $NR^7R^8$—$(CR^{14}R^{15})_n$—$NR^9R^{10}$, wherein $R^{14}$ and $R^{15}$ are independently H or alkyl or $R^{14}$ and $R^{15}$ groups, on the same carbon atom or on neighboring carbon atoms, are linked to form a carbocylic ring and n is an integer from 1 to 4. Preferably, $R^{14}$ and $R^{15}$ are both hydrogen and n is 2 or 3, more preferably 2. $R^7$, $R^8$, $R^9$ and $R^{10}$ are preferably H or methyl and, more preferably, all of $R^7$, $R^8$, $R^9$ and $R^{10}$ are H.

When $R^8$ is present in A, then p is 0. When $R^8$ is absent, then p is 1 and C' takes the place of $R^8$.

In a further aspect of the invention, $R^8$ is absent from A, p is 1 and C' is $C_4$ to $C_{10}$ straight chain alkylene (eg hexylene). Compounds according to this aspect of the invention are so-called dinuclear complexes comprising two ruthenium atoms per complex.

Other examples of dinuclear complexes of the invention are those in which pairs of A and B together with linker C' represent:

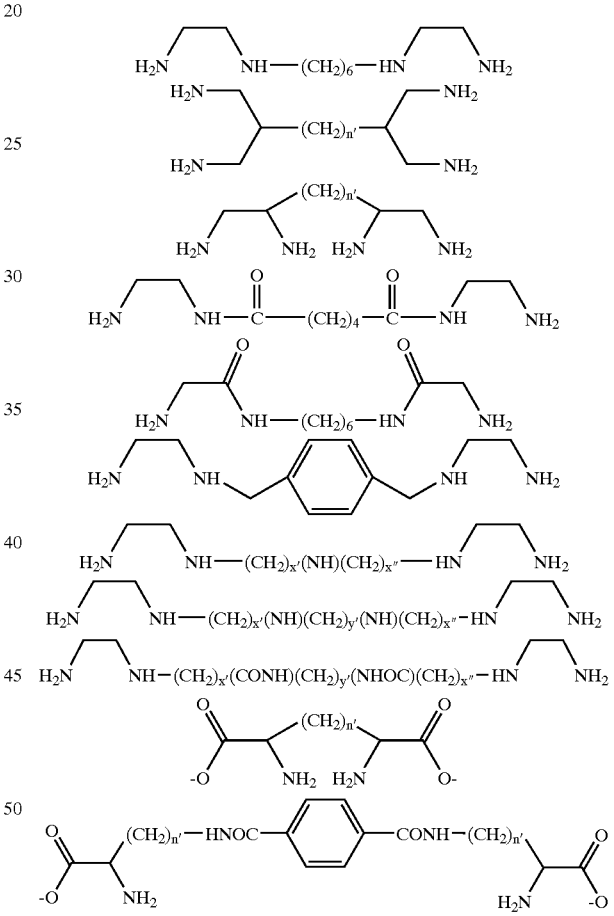

wherein each n', n", x', x" and y' independently represents an integer from 1 to 12, preferably 1 to 6.

$Y^{q-}$ in compounds of formula (I) is a counterion and is only present in the compound when the complex containing the metal ion is charged. $Y^{q-}$ is preferably a non-nucleophilic anion such as $PF_{6-}$, for example.

R' and R" are preferably alkyl. Most preferably, both R' and R" are methyl.

A particular sub-group of compounds of formula I, which may be active against resistant cell lines, are those in which $R_3$, $R_4$, $R_5$ and $R_6$ are all H, $R^1$ and $R^2$ together with the phenyl ring to which they are bound form an optionally hydrogenated anthracene ring system (such as $C_{14}H_{14}$ or $C_{14}H_{12}$), X is halo, A and B are N donor ligands, p is 0, r is 1, m is 1 and $Y^{q-}$ is a non-nucleophilic ion such as $PF_6^-$. Preferably, A and B are both NH2 groups linked by a $C_2$–$C_6$ alkylene chain, more preferably a $C_2$ alkylene chain ie, A and B together represent ethylenediamine.

Compounds of formula (I) may be used in medicine. In particular, compounds of formula (I) may be used to treat and/or prevent cancer.

Therefore, the present invention also provides the use of a compound of the invention (ie, a compound of formula (I)) in the manufacture of a medicament for the treatment and/or prevention of cancer.

Further provided by the invention is a method of treating and/or preventing cancer which comprises administering to a subject a therapeutically effective amount of a compound of the invention.

The compounds of the invention may be used directly against a tumour. Alternatively or additionally, the compounds may be used to prevent or inhibit metastasis and/or to kill secondary tumours. It will be understood that the prevention or inhibition of metastasis is encompassed by the term "preventing cancer", as used herein.

Compounds of the invention may be effective in treating and/or preventing tumours caused by cells that are resistant to other cytotoxic drugs, such as cis-platin, for example.

The invention also provides a pharmaceutical composition comprising one or more compounds of the invention together with one or more pharmaceutically acceptable excipients. Suitable excipients include diluents and/or carriers.

The compounds of the invention may be administered by a number of routes including, for example, orally, parenterally (eg, intramuscularly, intravenously or subcutaneously), topically, nasally or via slow releasing microcarriers. Thus, suitable excipients for use in the pharmaceutical compositions of the invention include saline, sterile water, creams, ointments, solutions, gels, pastes, emulsions, lotions, oils, solid carriers and aerosols.

The compositions of the invention may be formulated in unit or sub-unit dosage form including, for example, tablets, capsules and lozenges and containers containing the composition in a form suitable for parenteral administration.

The specific dosage level of the compounds and compositions of the invention will depend upon a number of factors, including the biological activity of the specific compound used and the age, body weight and sex of the subject. It will be appreciated that the subject may be a human or a mammalian animal.

The compounds and compositions of the invention can be administered alone or in combination with other compounds. The other compounds may have a biological activity which complements the activity of the compounds of the invention eg, by enhancing its effect in killing tumours or by reducing any side-effects associated with the compounds of the invention.

The present invention also provides a process for preparing the compounds of the invention which comprises the reaction of a compound of formula $[(\eta^6\text{-}C_6(R^1)(R^2)(R^3)(R^4)(R^5)(R^6))RuX_2]$, which may be in the form of a monomer or a dimer, with A and B, optionally in the presence of $Y^{q-}$, in a suitable solvent for the reaction, wherein $R^1$, $R^2$, $R^3$, $R^4$, $R^5$, $R^6$, X, A, B and Y are as defined above for the compounds of the invention.

Suitable compounds of formula $[(\eta^6\text{-}C_6(R^1)(R^2)(R^3)(R^4)(R^5)(R^6))RuX_2]$ for use as starting materials (starting ruthenium complexes) in the process of the invention include $[(\eta^6\text{-}C_{14}H_{14})RuCl_2]_2$, $[(\eta^6\text{-}C_{14}H_{14})RuBr_2]_2$, $[(\eta^6\text{-}C_{14}H_{14})RuI_2]_2$, $[(\eta^6\text{-}C_{14}H_{12})RuCl_2]_2$, $[(\eta^6\text{-}C_{14}H_{12})RuBr_2]_2$ and $[(\eta^6\text{-}C_{14}H_{12})RuI_2]_2$ which may be prepared according to the procedures herein disclosed.

When A and B in the compounds of the invention are $R^{11}$—CN, the solvent for the reaction may be $R^{11}$—CN itself. Preferred reaction conditions include stirring the starting ruthenium complex, as described above, in $R^{11}$—CN as solvent at 60° C. filtering off the $NH_4Cl$ precipitate formed and evaporating the filtrate to yield the product. The reaction mixture comprises a source of $Y^{q-}$, such as a compound of formula $(NH_4^+)Y^{q-}$ eg, $NH_4PF_6$.

Compounds of formula (I) in which A and B represent, together, $NR^7R^8$—$(CR^{14}R^{15})_n$—$NR^9R^{10}$ or $NR^9R^{10}$—$(CR^{14}R^{15})_n$—$NR^7$—C'—$NR^7$—$(CR^{14}R^{15})_n$—$NR^9R^{10}$ can be produced, according to the process of the invention, by stirring the starting ruthenium complex in the presence of a slight excess of $NR^7R^8$—$(CR^{14}R^{15})_n$—$NR^9NR^{10}$ or a molar equivalent amount of $NR^9R^{10}$—$(CR^{14}R^{15})_n$—$NR^7$—C'—$NR^7$—$(CR^{14}R^{15})_n$—$NR^9R^{10}$, respectively, in a suitable solvent, preferably an alcoholic solvent such as methanol. The reaction may be carried out at room temperature or at elevated temperature (eg, 30° C. to 90° C.) until a sufficient amount of product is formed; optionally after cooling the reaction mixture. The reaction mixture comprises a source of $Y^{q-}$, such as a compound of formula $(NH_4^+)Y^{q-}$ eg, $NH_4PF_6$.

Compounds of formula (I) in which A or B is an N-donor pyridine ligand may be obtained, according to the process of the invention, by heating a mixture of the starting ruthenium complex and excess pyridine compound (such as a 1.5- to 3-fold molar excess) in a suitable solvent such as benzene until a sufficient amount of product is formed. The reaction may be carried out under reflux conditions.

Compounds of formula (I) in which A or B is an S-donor sulfonyl ligand may be obtained, according to the process of the present invention, by dissolving the starting ruthenium complex in a solution of the sulfonyl compound, eg, dimethyl sulfoxide, and diffusing the resulting coloured solution with a suitable solvent, eg, diethyl ether.

The precipitate which is formed in the process of the invention comprises or consists of the compound of the invention, The compound of the invention may be isolated from the reaction mixture by separating the precipitate from the liquid phase (eg, by filtration) and then removing the solvent from the precipitate (eg, under reduced pressure). The solid thus formed, which comprises or consists of the compound of the invention may, optionally, be purified eg, by recrystallisation from a suitable solvent (including, for certain compounds of the invention, acetonitrile or acetonitrile/ether (where A and B are $R^{11}$—CN and $R^{11}$ is methyl) and methanol/ether).

The following non-limiting examples illustrate the present invention.

EXAMPLES

A. Synthesis

General

Ethylenediamine was freshly distilled over Na, ethanol and methanol dried over $P_2O_5$. Tetrahydrofuran (THF) was dried by distillation from Na-benzophenone.

Starting Materials

Preparation of 1,4,5,8,9,10-Hexahydroanthracene $(C_{14}H_{16})$[1]

Anthracene (4.0 g, 22.4 mmol) was dissolved in freshly dried THF (200 ml) and ethanol (40 ml). This mixture was added to liquid $NH_3$ (500 ml) which had been condensed under argon into a 1 litre flask equipped with a Dewar condenser, cooling bath (dry-ice/acetone) and mechanical stirrer. Sodium (10.40 g, 0.45 mol) was added in small pieces over a period of 20 min. After a further 50 min stirring at −60° C., the cooling bath was removed and the ammonia was allowed to evaporate under an argon flow with stirring. Into the residue was added 50 ml water slowly to decompose the excess of sodium and then a further 150 ml. This was extracted with diethyl ether (4×250 ml) and the combined ether layers washed with saturated NaCl solution (2×250 ml) and dried over $MgSO_4$. Removal of diethyl ether on the rotary evaporator afforded the white solid. Recrystallised (2×) first from benzene-chloroform (1:1) and then from benzene only to yield a white needle product, 98% pure by $^1$H NMR. This was used without further purification.

Yield: 1.54 g, 8.36 mmol, 37.3%

Preparation of 1,4,9,10-Tetrahydroanthracene $(C_{14}H_{14})$[2]

9,10-Dihydroanthracene (5.0 g, 27.74 mmol) dissolved in 300 ml THF was added to refluxing ammonia which had been condensed under argon into a 1 litre flask equipped with a Dewar condenser, cooling bath (dry-ice/acetone) and mechanical stirrer. Li wire (0.48 g, 69.35 mmol) was added in small pieces over a period of 20 min. After refluxing for 4 h with stirring, to the reaction mixture was added 60 ml ethanol and then 120 ml water and the ammonia allowed to evaporate. This was extracted with diethyl ether (2×250 ml) and the combined ether layers washed with saturated NaCl solution (1×250 ml) and dried over $MgSO_4$. Removal of ether on the rotary evaporator afforded a light yellow solid which was recrystallized (2×) from benzene to remove most of the hexahydroanthracene $(C_{14}H_{16})$ as white needles. Further recrystalliation from acetone yielded white plates of the tetrahydroanthracene $(C_{14}H_{14})$, 97% pure by $^1$H NMR. This was used without further purification.

Yield: 1.5 g, 8.23 mmol, 29.7%

Preparation of $[(\eta^6\text{-}C_{14}H_{14})RuCl_2]_2$[3]

1,4,5,8,9,10-Hexahydroanthracene (1.0 g, 5.43 mmol) was added to a filtered solution of $RuCl_3 3H_2O$ (0.84 g, 3.18 mmol) in dry ethanol (60 ml). The reaction was heated to reflux under argon for 48 hours. Filtration of the warm reaction mixture left a yellow-brown solid which was washed with a little ethanol, followed by diethyl ether (4×10 ml) and dried in vacuo.

Yield: 0.96 g, 1.36 mmol, 8.5%

Preparation of $[(\eta^6\text{-}C_{14}H_{12})RuCl_2]_2$ 1,4,9,10-Tetrahydroanthracene (0.45 g, 2.49 mmol) was added to a filtered solution of $RuCl_3 3H_2O$ (0.48 g, 1.83 mmol) in dry ethanol (45 ml). The reaction was heated to reflux under argon for 48 h. Filtration of the warm reaction mixture left a brown solid which was washed with a little ethanol, followed by diethyl ether (4×10 ml) and dried in vacuo.

Yield: 0.57 g, 0.81 mmol, 88.5%

Example 1

Preparation of $[(\eta^6\text{-}C_{14}H_{14})RuCl(en)]^+PF_6$ $[(\eta^6\text{-}C_{14}H_{14})RuCl_2]_2$ (0.205 g, 0.289 mmol) was stirred in dry methanol (25 ml) under argon at 60° C. Ethylenediamine (en) (48 μl, 0.75 mmol) was added in one portion. The reaction was stirred at 60° C. for 3 h and filtered and $NH_4PF_6$ (0.4 g, 2.45 mmol) added. The volume was reduced to approximately 6 ml on the rotary evaporator. After standing at 4° C. overnight, the yellow microcrystalline solid was collected, washed with a little methanol, followed by ether and dried in vacuo. This was recrystallised from methanol/ether.

Yield: 0.1 g, 0.19 mmol, 32.9%

$C_{16}H_{22}ClF_6N_2PRu(523.85)$ Calc.% C=36.68 %H=4.23 %N=5.35 Found %C=36.20 %H=4.17 %N=5.34

Example 2

Preparation of $[(\eta^6\text{-}C_{14}H_{14})RuCl_2(DMSO)]$[3]

$[(\eta^6\text{-}C_{14}H_{14})RuCl_2]_2$ (0.05 g, 0.07 mmol) was dissolved into dimethyl sulfoxide (2 ml) and filtered to yield a deep red solution. Slow diffusion of diethyl ether into this solution resulted in the formation of brilliant red crystals suitable for X-ray diffraction. The crystals were collected and washed thoroughly with diethyl ether (4×10 ml).

Yield: 0.03 g, 0.07 mmol, 49.5%

$C_{16}H_{20}Cl_2ORuS(432.37)$ Calc. %C=44.45 %H=4.66 Found %C=44.41 %H=4.51

Example 3

Preparation of $[(\eta^6\text{-}C_{14}H_{14})RuCl(CH_3CN)_2]^+PF_6^-$ $[(\eta^6\text{-}C_{14}H_{14})RuCl_2]_2$ (0.10 g, 0.144 mmol) was suspended in 10 ml acetonitrile. $NH_4PF_6$ (47.1 mg, 0.288 mmol) in 2 ml acetonitrile was added in one portion. The reaction was stirred at 60° C. without special precautions to exclude air. After 48 h the pale brown precipitate was filtered off and orange filtrate evaporated to yield an orange solid. This was recrystallized from acetonitrile/ether to yield orange crystals.

Yield: 0.13 g, 0.238 mmol, 82.8%

$C_{18}H_{20}ClF_6N_2PRu(545.86)$ Calc. %C=39.60 %H=3.69 %N=5. 13 Found %C=39.17 %H=3.48 %N=5.47

Example 4

Preparation of $[\eta^6\text{-}C_{14}H_{12})RuCl(en)]^+PF_6-$ $[(\eta^6\text{-}C_{14}H_{12})RuCl_2]_2$ (0.10 g, 0.142 MMol) was stirred in 10 ml dry methanol under argon at 60° C. Ethylenediamine (en) (24 μl, 0359 mmol) was added in one portion. The reaction was maintained at 60° C. with stirring for 5 h and filtered. The volume was reduced to approximately 4 ml on the rotary evaporator and then a solution of $NH_4PF_6$ (0.20 g, 1.227 mmol) in 2 ml methanol was added. A yellow solid precipitated from the mixed solution when briefly shaken. After standing at 4° C. overnight, this solid was collected, washed with a little methanol, followed by diethyl ether and dried in vacuo. This was recrystallised from benzylalcohol/ether.

Yield: 0.1 g, 0.19 mmol, 67.5%

$C_{16}H_{20}ClF_6N_2PRu(521.83)$ Calc. %C=36.82 %H=3.86 %N=5.37 Found %C=36.50 %H=3.85 %N=5.38

Example 5

Preparation of $[(\eta^6\text{-}C_{14}H_{12})RuCl_2(DMSO)]$ $[(\eta^6\text{-}C_{14}H_{12})RuCl_2]_2$ (0.05 g, 0.07 mmol) was dissolved into dimethyl sulfoxide (1 ml) and filtered to yield a rose red solution. Slow diffusion of diethyl ether into this solution resulted in the formation of brilliant red crystals suitable for X-ray diffraction. The crystals were collected and washed thoroughly with diethyl ether (3×10 ml).

Yield: 0.025 g, 0.058 mmol, 41.4%

$C_{16}, H_{18}Cl_2ORuS(430.35)$ Calc. %C=44.65 %H=4.21 Found %C=44.08 %H=4.18

Example 6

Preparation of $[(\eta^6\text{-}C_{14}H_{12})RuCl(CH_3CN)_2]^+PF_6^-$ $[(\eta^6\text{-}C_{14}H_{12})RuCl_2]_2$ (0.10 g, 0.142 mmol) was suspended in 10 ml acetonitrile. $NH_4PF_6$ (48.6 mg, 0.298 mmol) in 2 ml acetonitrile was added in one portion. The reaction was stirred at 60° C. without special precautions to exclude air. After 25 h the pale brown precipitate was filtered off and the orange filtrate evaporated to yield an orange solid. This was recrystallized from acetonitrile/ether to yield orange crystals.

Yield: 0.125 g, 0.23 mmol, 81%

$C_{18}H_{18}ClF_6N_2PRu(543.85)$ Calc. %C=39.75 %H=3.34 %N=5.15 Found %C=39.42 %H=3.33 %N=5.14

Example 7

Preparation of $\{[(\eta^6\text{-}C_{14}H_{14})RuCl]_2[H_2N(CH_2)_2NH(CH_2)_6NH(CH_2)_2NH_2\text{-}N,N'N'',N''']\}^{2+}.2PF_6^-$ The starting material $[(\eta^6\text{-}C_{14}H_{14})RuCl_2]_2$ was prepared as previously described. Ethylenediamine and triethylamine were freshly distilled over Na. Tetrahydrofuran (THP) was dried by distillation from Na-benzophenone. Triphenylmethyl chloride (99%) and adipoyl chloride (98%) were purchased from the Arcos Chemical Co. All other chemicals were AR grade and were used as received.

(a) N-tritylethyldiamine

A solution of trityl chloride (5.57 g, 20 mmol) in dichloromethane (25 ml) was slowly added into a solution of ethylenediamine (8 ml, 120 mmol) in dichloromethane (75 ml) with stirring at room temperature. The addition was accomplished within 1 h and the reaction stirred overnight. The white salt was filtered off and the filtrate washed with water and dried over anhydrous sodium sulphate. Dichloromethane was removed by rotary evaporation and the residue dissolved into methanol. A white precipitate began to form after shaking for a while and the mixture was kept in the refrigerator for 5 h and then filtered off. The methanol filtrate was reduced to 10 ml and kept in the refrigerator overnight. A white solid precipitated. This was collected as the desired product and washed with diethyl ether and dried in vacuo.

Yield: 4.5 g, 14.88 mmol, 74.4%

(b) N,N'-Bis(2'-tritylaminoethyl)-1,6-diamidohexane

N-Tritylethyldiarine (1.5 g, 4.96 mmol) and triethylamine (1.0 g, 7.29 mmol) were dissolved in chloroform (35 ml) and cooled in an ice bath. To this solution was added adipoyl chloride (0.36 ml, 2.48 mmol) in chloroform (10 ml) slowly with stirring. After addition, the mixture was refluxed for 2 h and cooled to room temperature. This was filtered to give a clear chloroform filtrate (see below). The filtered precipitate was dissolved into dichloromethane. This was washed with water and then saturated NaCl solution and dried over anhydrous sodium sulphate. Removal of the solvent by rotary evaporation gave a white product. The chloroform filtrate was also washed with water and saturated NaCl solution and dried over anhydrous sodium sulphate. After removal of chloroform, a further crop of product was obtained.

Yield: 1.40 g, 1.91 mmol, 77%

$C_{48}H_5O_2N_4H_2O(732.96)$ Calc. %C=78.66 %H=7.15 %N=7.64 Found %C=78.81 %H=6.73 %N=7.55

(c) N,N'-Bis(2'-tritylaminoethyl)-1,6-diaminohexainie

To a solution of N,N'-bis(2'-tritylaminoethyl)-1,6-diamidohexane (1.3 g, 1.82 mmol) in dry THF was added a suspension of $LiAlH_4$ (0.69 g, 18.18 mmol) in dry THF (20 ml) under argon with vigorous stirring. After the addition, the reaction was heated to a gentle reflux with stirring for 25 h. This was cooled to 4° C. The reaction product and excess hydride were decomposed by the dropwise addition of $H_2O$ (0.69 ml), followed by 15% (w/v) NaOH solution (0.69 ml) and $H_2O$ (2.07 ml) in succession. After vigorous stirring for 30 min, the mixture was filtered by suction and the resulting cake was washed thoroughly with dichloromethane. The combined filtrate was concentrated to dryness on the rotary evaporator and the resulting residue dissolved into dichloromethane (50 ml). This was washed with water and then saturated NaCl solution and dried over anhydrous sodium sulphate. Removal of dichloromethane by rotary evaporator afforded a colourless solid.

Yield: 1.20 g, 1.75 mmol, 96%

(d) N,N'-Bis(2-aminoethyl),1,6diaminohexane tetrahydrochloride

A mixture of N, N'-bis(2'-tritylaminoethyl)-1,6-diaminohexane (1.0 g 1.45 mmol) and 6 M HCl (30 ml) was refluxed for 3 h. The mixture was filtered and the filtrate was concentrated to about 3 ml over vacuao. Addition of methanol into the concentrated solution afforded a white salt.

Yield: 0.46 g, 1.32 mmol, 92%

$C_{10}H_{26}N_4.4HCl(348.09)$ Calc. %C=34.48 %H=8.68 %N=16.09 Found %C=34.26 %H=8.77 %N=16.24

(e) $\{[(\eta^6\text{-}C_{14}H_{14})RuCl]_2[H_2N(CH_2)_2NH(CH_2)_6NH(CH_2)_2NH_2\text{-}N,N',N'',N''']\}^{2+}.2PF_6^-$ $[(\eta^6\text{-}C_{14}H_{14})RuCl_2]_2$ (0.15 g, 0.213 mmol) in 10 ml methanol was stirred under argon at 60° C. To this suspension was added a solution of N,N'-bis(2-aminoethyl)-1,6-diaminehexane (0.213 mmol) in methanol which was obtained by treatment of N,N'-bis(2-aminoethyl)1,6-diaminehexane tetrahydrochloride (73.97 g, 0.213 mmol) with 1.697 ml 0.5008 N KOH-MeOH solution. The mixture was stirred at 60° C. for a further 1.5 h. This was filtered while hot and concentrated to 6 ml. Addition of $NH_4PF_6$ (0.25 g; 1.53 mmol) to the concentrated solution afforded a yellow precipitate. This was recrystallized from methanol/ether.

Yield: 0.09 g, 0.0796 mmol, 37.4%

$C_{38}H_{54}Cl_2F_{12}N_4P_2RU_2(1129.85)$ Calc. %C=40.39 %H=4.81 %N=4.9 Found %C=40.30 %H=4.49 %N=4.21

B. Biological Data

1. Protocol for Testing Ru Compounds

The compounds are tested on 24-well trays. Cells growing in a flask are harvested just before they become confluent, counted using a haemocytometer and diluted down with media to a concentration of $1\times10^4$ cells per ml. The cells are then seeded in the 24-well trays at a density of $10\times10^4$ cells per well (i.e. 1 ml of the diluted cell suspension is added to each well). The cells are then left to plate down and grow for 72 hours before adding the compounds of the invention.

The Ru complexes are weighed out and made up to a concentration of is 1 mg/ml with deionised water then sonicated, until they go into solution. The appropriate volume of the Ru solution is added to 5 ml of media to make it up to a concentration of 100 $\mu$M for each drug. This 100 $\mu$M solution is then serially diluted to make up the 10 $\mu$M, 1 $\mu$M and 0.1 $\mu$M solutions.

The media is removed from the cells and replaced with 1 ml of the media dosed with drug. Each concentration is done in duplicate. A set of control wells are left on each plate, containing media without drug.

The cells are left exposed to the drugs for 24 hours and then washed with phosphate buffered saline before fresh media is added.

They are allowed to grow on for a further 3 days before being counted using a Coulter counter.

Preparing Cells for Counting:

Media is removed and 1 ml of PBS is added to the cells.

250 $\mu$l of trypsin is added and cells left in incubator for a few minutes to allow the monolayers to detach.

Once trypsinised, 250 $\mu$l of media is added to each well to neutralise the trypsin. 200 $\mu$l of this suspension is added to 10 ml of NaCl for counting.

2. Results

Using the above protocol, a number of compounds of the invention were tested on A2780 ovarian cancer cell line. The results are as follows:

| Compound (Example No.) | IC50 ($\mu$M) |
|---|---|
| 1 | 0.5 |
| 2 | 94 |
| 3 | 177 |
| 4 | 0.3 |
| 5 | 68 |
| 6 | 315 |
| 7 | 6 |

The experiments were repeated to investigate the effect of the compounds of the invention on drag-resistant variants of the A2780 cell line. The following results were obtained:

| Compound (Example No.) | IC50 ($\mu$M) | | |
|---|---|---|---|
| | A2780 | A2780 cis* | A2780 AD** |
| 1 | 0.5 | 1 | 328 |
| 2 | 94 | 493 | 4 |
| 3 | 116 | 2 | 2 |
| 4 | 2 | 16 | 104 |
| 5 | 126 | 2 | 5 |
| 6 | 192 | 2 | 0.9 |

*Variant of A2780 showing resistance to cis-platin
**Variant of A2780 showing resistance to adriomycin. This cell line is a multidrug resistant cell line that over expresses the p glycoprotein.

Compounds of the invention therefore have cytotoxicity against cancer cells that are resistant to treatment by other drugs.

REFERENCES

[1] A. J. Birch, P. Fitton, D. C. C. Smith, D. E. Steere, A. R. Stelfox J. Chem. Soc. 1963, 2209–2216
[2] R. G. Harvey J. Org. Chem. 1967, 32, 238
[3] T. J. Beasley, R. D. Brost, C. K. Chu, S. L. Grundy, S. R. Stobart Organometallics 1993, 12, 4599–4606

What is claimed is:

1. A method for treating cancer comprising administering to a subject a therapeutically effective amount of a ruthenium (II) compound of formula (I):

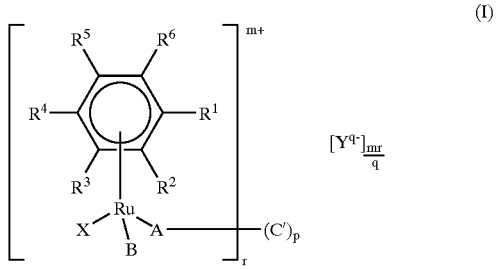

wherein $R^1$ and $R^2$ together with the ring to which they are bound represent a saturated or unsaturated carbocyclic or heterocyclic group containing up to three 3- to 8- membered carbocyclic or heterocyclic rings, wherein each carbocyclic or heterocyclic ring may be fused to one or more other carbocyclic or heterocyclic rings; and wherein each of the rings may be optionally substituted by one or more groups independently selected from alkyl, aryl, alkaryl, halo, carboxy, carboxyester, carboxyamide, sulfonate, sulfonamido or alkether; $R^3$, $R^4$, $R^5$ and $R^6$ independently represent H, alkyl, —$CO_2R'$, aryl or alkaryl, which latter two groups are optionally substituted on the aromatic ring; R' represents alkyl, aryl or alkaryl;

X is halo, $H_2O$, (R') (R'') S(O), R' $CO_2^-$ or (R') (R'')C=O, where R'' represents alkyl, aryl or alkaryl;

Y is a counterion;

m is 0 or 1;

q is 1, 2 or 3;

C' is $C_1$ to $C_{12}$ alkylene, optionally substituted in or on the alkylene chain, bound to two A groups;

p is 0 or 1 and r is 1 when p is 0 and r is 2 when p is 1; and

A and B are each independently O-donor, N-donor or S-donor ligands and one of A and B may be halo, or wherein if p is 0, A and B optionally together represent $NR^7R^8$—$(CR^{14}R^{15})_n$—$NR^9R^{10}$, wherein $R^7$, $R^8$, $R^9$ and $R^{10}$ independently represent H or alky, $R^{14}$ and $R^{15}$ are hydrogen, or are linked at the same or neighbouring carbon atoms to form a carbocylic ring, and n is an interger from 1 to 4, and wherein if p is 1, A and B may together represent $NR^7$—$(CR^{14}R^{15})_n$—$NR^9R^{10}$.

2. The method of claim 1, wherein $R^3$, $R^4$, $R^5$ and $R^6$ all represent H.

3. The method of claim 1 or claim 2, wherein $R^1$ and $R^2$ together with the ring to which they are bound represent anthracene.

4. The method claim 3, wherein $R^1$ and $R^2$ together with the ring to which they are bound represent 1,4-dihydroanthracene.

5. The method claim 3, wherein $R^1$ and $R^2$ together with the ring to which they are bound represent 1,4,9,10-tetrahydroanthracene.

6. The method claim 1, wherein A and B are both $R^{11}$—CN and $R^{11}$ represents alkyl.

7. The method claim 1, wherein one of A and B is a $R^{12}R^{13}S(O)$ group and the other is halo.

8. The method claim 1, wherein if p is 0, A and B together represent $NR^7R^8$—$(CR^{14}R^{15})_n$—$NR^9R^{10}$, wherein $R^7$, $R^8$, $R^9$ and $R^{10}$ independently represent H or alkyl, $R^{14}$ and $R^{15}$ are hydrogen, or are linked at the same or neighbouring carbon atoms to form a carbocylic ring, and n is an integer from 1 to 4, and wherein if p is 1, A and B together represent $NR^7$—$(CR^{14}R^{15})_n$—$NR^9R^{10}$.

9. The method of claim 8, wherein $R^7$, $R^8$, $R^9$ and $R^{10}$ all represent H.

10. The method of claim 8, wherein $R^{14}$ and $R^{15}$ are both H and n is 2.

11. The method claim 8, wherein p is 0.

12. The method claim 8, wherein $R^8$ is absent, p is 1 and C' is $C_4$ to $C_{10}$ straight chain alkylene.

13. Ruthenium (II) compound of formula (II):

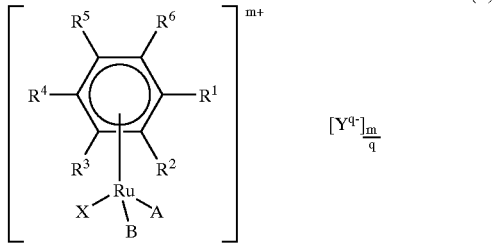

wherein $R^1$ and $R^2$ together with the ring to which they are bound represent anthracene or a mono, di or tri hydrogenated derivative of anthracene; and wherein each of the rings may be optionally substituted by one or more groups indepently selected from alkyl, aryl, alkaryl, halo, carboxy, carboxyester, carboxyamide, sulfonate, sulfonamido or alkether;

$R^3$, $R^4$, $R^5$ and $R^6$ independently represent H, alkyl, —$CO_2R'$, aryl or alkaryl, which latter two groups are optionally substituted on the aromatic ring;

R' represents alkyl, aryl or alkaryl;

X is halo, $H_2O$, (R') (R") S(O), R' $CO_2^-$ or (R') (R")C=O, where R" represents alkyl, aryl or alkaryl;

Y is a conterion;

m is 0 or 1;

q is 1,2 or 3; and

A and B are each independently O-donor, N-donor or S-donor ligands and one of A and B may be halo, or A and B may together represent $NR^7R^8$—$(CR^{14}R^{15})_n$—$NR^9R^{10}$, wherein $R^7$, $R^8$, $R^9$ and $R^{10}$ independently represent H or alkyl, $R^{14}$ and $R^{15}$ are hydrogen, or are linked at the same or neighbouring carbon atoms to form a carbocylic ring, and n is an integer from 1 to 4.

14. Compound as claimed in claim 13, wherein $R^1$ and $R^2$ together with the ring to which they are bound represent anthracene.

15. Compound as claimed in claim 13, wherein $R^1$ and $R^2$ together with the ring to which they are bound represent 1,4-dihydroanthracene.

16. Compound as claimed in claim 13, wherein A and B are both $R^{11}$—CN and $R^{11}$ represents alkyl.

17. Compound as claimed in claim 13, wherein one of A and B is a $R^{12}R^{13}S(O)$ group and the other is halo.

18. Ruthenium (II) compound of formula (III):

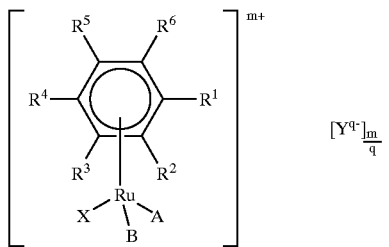

(III)

wherein $R^1$ and $R^2$ together with the ring to which they are bound represent a saturated or unsaturated carbocyclic or heterocyclic group containing up to three 3-to 8-membered carbocyclic or heterocyclic rings, wherein each carbocyclic or heterocyclic ring may be fused to one or more other carbocyclic or heterocyclic rings; and wherein each of the rings may be optionally sustituted by one or more groups independently selected from alkyl, aryl, alkaryl, halo, carboxy, carboxyester, carboxyamide, sulfonate, sulfonamido or alkether;

$R^3$, $R^4$, $R^5$ and $R^6$ independently represent H, alkyl, —$CO_2R'$, aryl or alkaryl, which latter two groups are optionally substituted on the aromatic ring;

R' represents alkyl, aryl or alkaryl;

X is halo, $H_2O$, (R') (R") S(O), R' $CO_2^-$ or (R')(R")C=O, where R" represents alkyl, aryl or alkaryl;

Y is a counterion;

m is 0 or 1;

q is 1,2 or 3;

wherein A and B together represent $NR^7R^8$—$(CR^{14}R^{15})_n$—$NR^9R^{10}$, wherein $R^{14}$ and $R^{15}$ are hydrogen, or are linked at the same or neighbouring carbon atoms to form a carbocylic ring, and n is an integer from 1 to 4.

19. Compound as claimed in claim 18, wherein $R^1$ and $R^2$ together with the ring to which they are bound represent [1,4,9,10-tetrahydro]anthracene.

20. Compound as claimed in claim 18, wherein $R^7$, $R^8$, $R^9$ and $R^{10}$ all represent H.

21. Compound as claimed in claim 18, wherein $R^{14}$ and $R^{15}$ are both H and n is 2.

22. Ruthenium (II) compound of formula (IV):

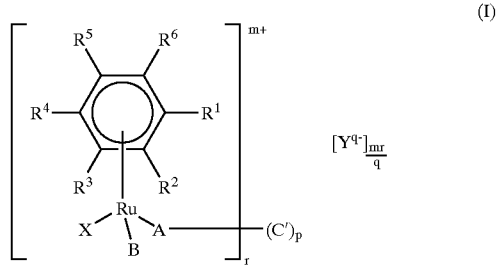

(I)

wherein $R^1$ and $R^2$ together with the ring to which they are bound represent a saturated or unsaturated carbocyclic or heterocyclic group containing up to three 3-to 8-membered carbocyclic or heterocyclic rings, wherein each carbocyclic or heterocyclic ring may be fused to one or more other carbocyclic or heterocyclic rings; and wherein each of the rings may be optionally substituted by one or more groups independently selected from alkyl, aryl, alkaryl, halo, carboxy, carboxyester, carboxyamide, sulfonate, sulfonamido or alkether;

$R^3$, $R^4$, $R^5$ and $R^6$ independently represent H, alkyl, —$CO_2R'$, aryl or alkaryl, which latter two groups are optionally substituted on the aromatic ring;

R' represents alkyl, aryl or alkaryl;

X is halo, $H_2O$, (R') (R")S(O),$R'CO_2$ or (R')(R")C=O, where R" represents alkyl, aryl or alkaryl;

Y is a counterion;

m is 0 or 1;

q is 1,2 or 3;

C' is $C_1$ to $C_{12}$ alkylene, optionally substituted in or on the alkylene chain, bound to two A groups;

p is 1 and r is 2; and

A and B are each independently O-donor, N-donor or S-donor ligands and one of A and B may be halo, or wherein A and B optionally together represent $NR^7$—$(CR^{14}R^{15})_n$—$NR^9R^{10}$, wherein $R^7$, $R^9$ and $R^{10}$ independently represent H or alkyl, $R^{14}$ and $R^{15}$ are hydrogen, or are linked at the same or neighbouring carbon atoms to form a carbocylic ring, and n is an integer from 1 to 4.

23. Compound as claimed in claim 22, wherein $R^1$ and $R^2$ together with the ring to which they are bound represent anthracene.

24. Compound as claimed in claim 22, wherein $R^1$ and $R^2$ together with the ring to which they are bound represent 1,4-dihydroanthracene.

25. Compound as claimed in claim 22, wherein $R^1$ and $R^2$ together with the ring to which they are bound represent 1,4,9,10-tetrahydroanthracene.

26. Compound as claimed in claim 22, wherein A and B together represent $NR^7R^8$—$(CR^{14}R^{15})_n$—$NR^9R^{10}$, wherein $R^{14}$ and $R^{15}$ are hydrogen, or are linked at the same or neighbouring carbon atoms to form a carocylic ring, and n is an integer from 1 to 4.

27. Compound as claimed in claim 26, wherein C' is $C_4$ to $C_{10}$ straight chain alkylene.

28. Compound as claimed in claim 26, wherein $R^7$, $R^8$, $R^9$ and $R^{10}$ all represent H.

29. Compound as claimed in claim 26, wherein $R^{14}$ and $R^{15}$ are both H and n is 2.

30. Compound as claimed in claim 13, claim 21 or claim 22, wherein $R^3$, $R^4$, $R^5$ and $R^6$ all represent H.

31. Process for preparing the compound of claim 13, which comprises the reaction of a compound of formula $[(\eta^6-C_6(R^1)(R^2)(R^3)(R^4)(R^5)(R^6))\,RuX_2]$, optionally in the form of a dimer, with A and B, optionally in the presence of $Y^{q-}$, in a suitable solvent for the reaction, wherein $R^1$, $R^2$, $R^3$, $R^4$, $R^5$, $R^6$, X, A, B, q and Y are as defined in claim 13.

32. Process for preparing the compound of claim 18, which comprises the reaction of a compound of formula $[(\eta^6-C_6(R^1)(R^2)(R^3)(R^4)(R^5)(R^6))RuX_2]$, optionally in the form of a dimer, with A and B, optionally in the presence of $Y^{q-}$, in a suitable solvent for the reaction, wherein $R^1$, $R^2$, $R^3$, $R^4$, $R^5$, $R^6$, X, A, B, q and Y are as defined in claim 18.

33. Process for preparing the compound of claim 22, which comprises the reaction of a compound of formula $[(\eta^6-C_6(R^1)(R^2)(R^3)(R^4)(R^5)(R^6))RuX_2]$, optionally in the form of a dimer, with A and B, optionally in the presence of $Y^{q-}$, in a suitable solvent for the reaction, wherein $R^1$, $R^2$, $R^3$, $R^4$, $R^5$, $R^6$, X, A, B, q and Y are as defined in claim 22.

34. The method of claim 1 wherein the cancer is ovarian cancer.

35. Ruthenium (II) compound of formula (I):

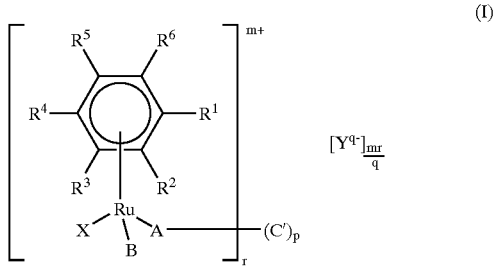

(I)

wherein $R^1$ and $R^2$ together with the ring to which they are bound represent a saturated or unsaturated carbocyclic or heterocyclic group containing up to three 3-to 8-membered carbocyclic or heterocyclic rings, wherein each cargocyclic or heterocyclic ring may be fused to one or more other carbocyclic or heterocyclic rings; and wherein each of the rings may be optionally substituted by one or more groups independently selected from alkyl, aryl, alkaryl, halo, carboxy, carboxyester, carboxyamide, sulfonate, sulfonamido or alkether;

$R^3$, $R^4$, $R^5$ and $R^6$ independently represent H, alkyl, —$CO_2R'$, aryl or alkarly, which latter two groups are optionally substituted on the aromatic ring;

R' represents alkyl, aryl or alkaryl;

X is halo, $H_2O$, (R')(R") S(O), R' $CO_2^-$ or (R')(R")C=O, where R" represents alkyl, aryl or alkaryl;

Y is a counterion;

m is 0 or 1;

q is 1,2 or 3;

C' is $C_1$ to $C_{12}$ alkylene, optionally substituted in or on the alkylene chain, bound to two A groups;

p is 0 or 1 and r is 1 when p is 0 and r is 2 when p is 1; and

A and B are each independently O-donor, N-donor or S-donor ligands and one of A and B may be halo, wherein if p is 0, A and B together represent $NR^7R^8$—$(CR^{14}R^{15})_n$—$NR^9R^{10}$, wherein $R^7$, $R^8$, $R^9$ and $R^{10}$ independently represent H or alkyl, $R^{14}$ and $R^{15}$ are hydrogen, or are linked at the same or neighbouring carbon atoms to form a carbocyclic ring, and n is an integer from 1 to 4, and wherein if p is 1, A and B together represent $NR^7$—$(CR^{14}R^{15})_n$—$NR^9R^{10}$.

36. Compound as claimed in claim 35, wherein $R^7$, $R^8$, $R^9$ and $R^{10}$ all represent H.

37. Compound as claimed in claim 35, wherein $R^{14}$ and $R^{15}$ are both H and n is 2.

38. Compound as claimed in claim 35, wherein p is 0.

39. Compound as claimed in claim 35, wherein $R^8$ is absent, p is 1 and C' is $C_4$ to $C_{10}$ staight chain alkylene.

40. A pharmaceutical composition comprising a ruthenium (II) compound of formula (I):

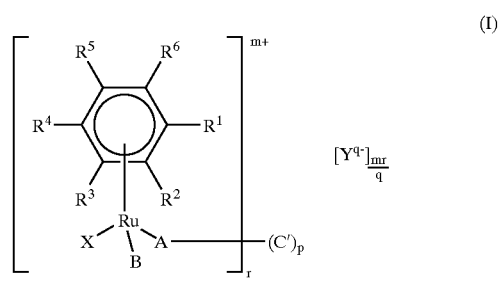

(I)

wherein $R^1$ and $R^2$ together with the ring to which they are bound represent a saturated or unsaturated carbocyclic or heterocyclic group containing up to three 3-to 8-membered carbocyclic or heterocyclic rings, wherein each carbocyclic or heterocyclic ring may be fused to one or more other carbocyclic or heterocyclic rings; and wherein each of the rings may be optionally substituted by one or more groups independently selected from alkyl, aryl, alkaryl, halo, carboxy, carboxyester, carboxyamide, sulfonate, sulfonamido or alkether;

$R^3$, $R^4$, $R^5$ and $R^6$ independently represent H, alkyl, —$CO_2R'$, aryl or alkaryl, which latter two groups are optionally substituted on the aromatic ring;

R' represents alkyl, aryl or alkaryl;

X is halo, $H_2O$, (R')(R") S(O), R' $CO_2^-$ or (R')(R")C=O, where R" represents alkyl, aryl or alkaryl;

Y is a counterion;

m is 0 or 1;

q is 1,2 or 3;

C' is $C_{12}$ alkylene, optionally substituted in or on the alkylene chain, bound to two A groups;

p is 0 or 1 and r is 1 when p is 0 and r is 2 when p is 1; and

A and B are each independently O-donor, N-donor or S-donor ligands and one of A and B may be halo, wherein if p is 0, A and B optionally together represent $NR^7R^8$—$(CR^{14}R^{15})_n$—$NR^9R^{10}$, wherein $R^7$, $R^8$, $R^9$ and $R^{10}$ independently represent H or alkyl, $R^{14}$ and $R^{15}$ are hydrogen, or are linked at the same or neighbouring carbon atoms to form a carbocyclic ring, and n is an integer from 1 to 4, and wherein if p is 1, A and B may together represent $NR^7$—$(CR^{14}R^{15})_n$—$NR^9R^{10}$ and a pharmaceutically acceptable excipient.

41. Pharmaceutical composition as claimed in claim 40, wherein $R^3$, $R^4$, $R^5$ and $R^6$ all represent H.

42. Pharmaceutical composition as claimed in claim 40 or claim 41, wherein $R^1$ and $R^2$ together with the ring to which they are bound represent anthracene.

43. Pharmaceutical composition as claimed in claim 42, wherein $R^1$ and $R^2$ together with the ring to which they are bound represent 1,4-dihydroanthracene.

44. Pharmaceutical composition as claimed in claim 43, wherein $R^1$ and $R^2$ together with the ring to which they are bound represent 1,4,9,10-tetrahydroanthracene.

45. Pharmaceutical composition as claimed in claim 40, wherein A and B are both $R^{11}$—CN and $R^{11}$ represents alkyl.

46. Pharmaceutical composition as claimed in claim 40, wherein one of A and B is a $R^{12}R^{13}S(O)$ group and the other is halo.

47. Pharmaceutical composition as claimed in claim 40, wherein if p is 0, A and B together represent $NR^7R^8$—$(CR^{14}R^{15})_n$—$NR^9R^{10}$, wherein $R^7$, $R^8$, $R^{10}$ independently represent H or alkyl, $R^{14}$ and $R^{15}$ are hydrogen, or are linked at the same or neighbouring carbon atoms to form a carbocylic ring, and n is an integer from 1 to 4, and wherein if p is 1, A and B together represent $NR^7$—$(CR^{14}R^{15})_n$—$NR^9R^{10}$.

48. Pharmaceutical composition as claimed in claim 47, wherein $R^7$, $R^8$, $R^9$ and $R^{10}$ all represent H.

49. Pharmaceutical composition as claimed in claim 47, wherein $R^{14}$ and $R^{15}$ are both H and n is 2.

50. Pharmaceutical composition as claimed in claim 47, wherein p is 0.

51. Pharmaceutical composition as claimed in claim 47, wherein $R^8$ is absent, p is 1 and C' is $C_4$ to $C_{10}$ straight chain alkylene.

* * * * *